(12) United States Patent
Hall et al.

(10) Patent No.: US 10,888,278 B2
(45) Date of Patent: *Jan. 12, 2021

(54) METHOD OF MONITORING HEALTH WHILE USING A TOILET

(71) Applicant: Medic, Inc., Provo, UT (US)

(72) Inventors: David R. Hall, Provo, UT (US); Dan Allen, Springville, UT (US); Ben Swenson, Lehi, UT (US); H. Tracy Hall, Provo, UT (US)

(73) Assignee: Hall Labs, LLC, Provo, UT (US)

( * ) Notice: Subject to any disclaimer, the term of this patent is extended or adjusted under 35 U.S.C. 154(b) by 173 days.

This patent is subject to a terminal disclaimer.

(21) Appl. No.: 15/215,008

(22) Filed: Jul. 20, 2016

(65) Prior Publication Data
US 2018/0020984 A1 Jan. 25, 2018

(51) Int. Cl.
*A61B 5/00* (2006.01)
*A47K 13/24* (2006.01)
*A61N 1/39* (2006.01)
*A47K 17/00* (2006.01)
*A61B 5/0205* (2006.01)
*A61B 5/0402* (2006.01)
*A61B 7/04* (2006.01)
*A61B 8/00* (2006.01)
(Continued)

(52) U.S. Cl.
CPC ............ *A61B 5/6891* (2013.01); *A47K 13/24* (2013.01); *A47K 17/00* (2013.01); *A61B 5/0059* (2013.01); *A61B 5/02055* (2013.01); *A61B 5/0402* (2013.01); *A61B 5/6806* (2013.01); *A61B 5/7282* (2013.01); *A61B 5/742* (2013.01); *A61B 5/7405* (2013.01); *A61B 5/7455* (2013.01); *A61B 7/04* (2013.01); *A61B 8/00* (2013.01); *A61N 1/39* (2013.01); *A61N 1/3904* (2017.08); *A61N 1/3993* (2013.01); *A61B 5/01* (2013.01); *A61B 5/053* (2013.01); *A61B 5/6823* (2013.01); *A61B 5/6831* (2013.01); *A61B 5/6888* (2013.01); *A61B 5/6894* (2013.01); *A61B 2562/0261* (2013.01)

(58) Field of Classification Search
CPC .... A61B 5/6887; A61B 5/6891; A61B 5/6806
See application file for complete search history.

(56) References Cited

U.S. PATENT DOCUMENTS

| | | | | |
|---|---|---|---|---|
| 4,697,656 A | * | 10/1987 | de Canecaude | G01G 19/44 177/144 |
| 5,738,112 A | * | 4/1998 | Brod | A47K 17/02 128/869 |

(Continued)

*Primary Examiner* — Eric D. Bertram

(57) ABSTRACT

A method of obtaining health data of a toilet user using one or more sensors is disclosed. One or more sensors are used by a toilet user while the toilet user is using the toilet to take health measurement readings of the user. Dynamic heart stress readings may be obtained and monitored over weeks, months and years. Rolling averages of heart function and heart health may be determined and deviations from the rolling averages may trigger notifications. Other health related measurements and functions such as temperature, respirations, heart rate, electrocardiogram, echocardiogram, and stethoscope sounds are also recorded and stored for trending and data analysis.

21 Claims, 13 Drawing Sheets

(51) Int. Cl.
*A61B 5/01* (2006.01)
*A61B 5/053* (2006.01)

(56) References Cited

U.S. PATENT DOCUMENTS

| | | | | |
|---|---|---|---|---|
| 7,194,776 B1* | 3/2007 | Lastuka | ................. | E03D 13/00 |
| | | | | 340/603 |
| 2005/0267536 A1* | 12/2005 | Freeman | ................ | A61N 1/046 |
| | | | | 607/5 |
| 2010/0241181 A1* | 9/2010 | Savage | ................. | A61N 1/046 |
| | | | | 607/5 |
| 2015/0196209 A1* | 7/2015 | Morris | ............... | A61B 5/02141 |
| | | | | 600/480 |
| 2016/0058287 A1* | 3/2016 | Dyell | ................... | A61B 5/0024 |
| | | | | 340/870.07 |
| 2016/0374619 A1* | 12/2016 | Borkholder | .......... | A61B 5/6891 |
| | | | | 600/301 |
| 2017/0354373 A1* | 12/2017 | Kostic | .................. | A61B 5/0006 |
| 2018/0000417 A1* | 1/2018 | Hall | ..................... | A61B 5/6831 |

* cited by examiner

METHOD OF MONITORING HEALTH WHILE USING A TOILET

BACKGROUND

Field of the Invention

This invention relates to medical toilets for taking health measurements of a user while using a toilet.

Background of the Invention

Using a toilet is for some the hardest work they will do in the course of a day. Torso measurements for health include stethoscope, EKG, and echocardiogram. However, known toilets do not provide access to a user's torso, only the back side of a user and the back of their legs.

SUMMARY

A toilet is dynamically useful for obtaining health-related measurements because of its frequency of use and because of the exertion required to relieve a body of waste. Toilets are used in a private location with frequent user body contact. A toilet with one or more torso sensors is disclosed. One or more torso sensors are used by a toilet user while the toilet user is using the toilet to take health measurement readings of the user. Dynamic heart stress readings may be obtained and monitored over weeks, months and years. Rolling averages of heart function and heart health may be determined and deviations from the rolling averages may trigger notifications. Other health related measurements and functions such as temperature, blood pressure, respirations, heart rate, electrocardiogram, echocardiogram, and stethoscope sounds are also recorded and stored for trending and data analysis.

One or more torso sensors may be arranged to place the sensors centered on or near the heart and lungs of a toilet user. The present invention provides a toilet with a torso strap, belt, glove or wand with health sensors. Users can wrap belt, position a wand, or place a glove across or on their torso for example from their shoulder to their opposite hip, or across their torso and under both armpits.

A belt may have a height adjustment mechanism to compensate for users of different height. The height adjustment can be done automatically via a motorized actuator based on a measured height or user profile or set manually. The belt may have an auto-tensioner. The tensioner such as an elastomer or coil spring provides positive connection force for the torso sensors and optionally hold a user's back steady against the turned up lid of the toilet, which may have additional sensors such as microphones to listen for lung congestion. The tensioner may allow the user to lean forward in aid of using the toilet without losing contact with toilet lid and the sensors.

A glove or wand may have one or more torso sensors attached to obtain health readings of a user. A toilet processor may instruct a user to take multiple readings at different locations on a torso of a user.

A display may instruct a user how to hold a wand, glove or position a belt against the user's torso to enable accurate measurements. The toilet user may be visually and/or audibly notified when the sensors are in proper position and obtaining acceptable readings. The toilet processor may instruct a toilet user to increase pressure between the sensors and the user's torso or the pressure may increase automatically through auto-tensioning of a belt. Sensors may include an ultrasound imager used in echocardiograms. Sensors may additionally include electrode sensors, microphone sensors, acoustic sensors, ultrasound sensors, motion sensors, strain sensors, optical sensors, temperature sensors, electrocardiogram (ECG or EKG) sensors, and/or stethoscope sensors. Strain sensors, motion sensors, electrode sensors, or sound sensors may also be included on, around or in a glove, wand to torso strap. One or more torso sensors may be used to detect bowel movement event.

The user may operate the one or more torso sensors to obtain personal measurements or be instructed to do so by a directing health care professional or mobile device application when advisable.

Frontal body EKG measurements have standard electrode placement locations for diagnostic EKG purposes. These provide additional information over what can be obtained from a hand-to-hand EKG measurement. Additionally, because a toilet provides contact with the thigh, a driven-right-leg EKG electrode can be provided in the toilet seat. Driven right leg has benefits for obtaining a higher quality EKG signal by controlling the body potential relative to the sensor.

In an example the user connects the belt at their hip and the toilet moves the belt connection point higher from the hip upwards toward the left armpit to wrap the belt around the heart region, then returns to the original position for ease of removal after the measurement is complete. In another example, the belt is provided with a defibrillator for a remote, physician-supervised cardio vert procedure, or an automated external defibrillator (AED) for emergency use. A stethoscope or multiple stethoscopes—basically microphones in contact with the body—attached to the belt can measure the sound of heart valves and blood flow.

In another example, the user may employ a hand held device such as a glove or wand comprising the sensors. The device may be moved to locations on the torso appropriate for the measurements to be taken. The device may be in communication the processor that records the measurements and transmits the measurements to a display. The processor may also direct the proper placement of hand device to achieve optimal measurements.

A toilet provides many benefits over a standard seat for taking health measurements. For example, a toilet provides a private location where a user may remove his or her shirt for obtaining direct skin contact sensor readings. Additionally, a toilet is used multiple times a day prompting routine data collection. A toilet also provides a natural stress on the heart while passing waste into the toilet enabling dynamic stress readings indicative of heart problems and blood flow problems.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

It will be readily understood that the components of the present invention, as generally described and illustrated in the Figures herein, may be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings.

Figure 1:
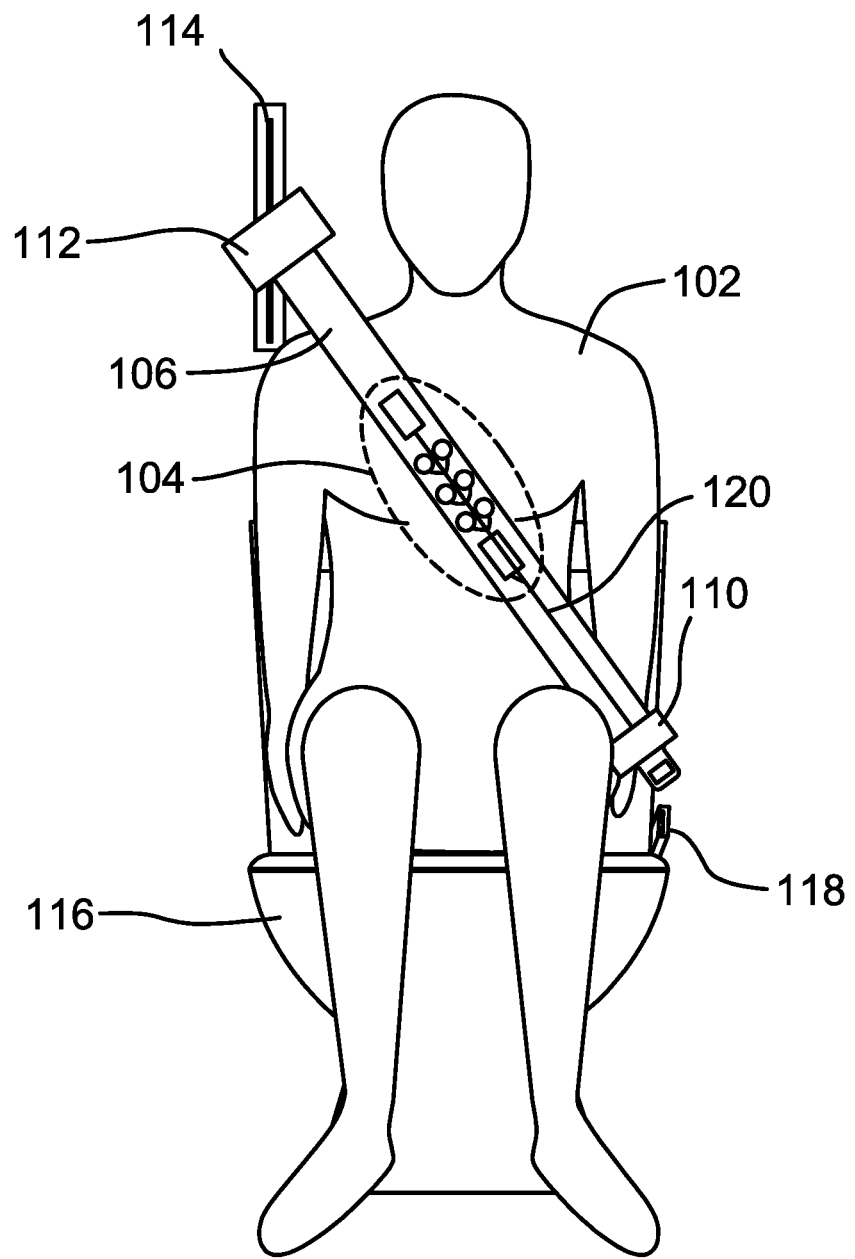
FIG. 1 is a front view of a toilet user sitting on a toilet with one or more torso sensors in accordance with an embodiment of the invention.

FIG. 1 shows a toilet user 102 sitting on a toilet 116 with a one or more sensors 104 diagonally pulled across the user's torso. One or more sensors 104 are used for measuring the user while the user is sitting on the toilet or while the user is using the toilet. The sensors 104 may comprise electrode sensors, microphone sensors, acoustic sensors, ultrasound sensors, motion sensors, strain sensors, optical sensors, temperature sensors, electrocardiogram (ECG or EKG) sensors, and stethoscope sensors. The sensors may receive data for determining a user's temperature, blood pressure, respirations, heart rate, electrocardiogram, echocardiogram, and stethoscope sounds. A controller or processor may be coupled to the sensors and programmed to determine one or more of: a user's temperature, respirations, heart rate, electrocardiogram, echocardiogram, and stethoscope sounds from the data received from the one or more sensors. The processor in the controller may interact with a toilet user. Such interaction may include voice recognition of a toilet user allowing a toilet user to provide data inputs by way of speaking. For instance, if a toilet user wanted to know what their heart rate is while using the toilet, the user may ask for their heart rate. The controller may cause a visual displaying or an audible speaking the heart rate of the toilet user. The controller may detect a toilet user by optical sensors, motion sensors, microphones, voice recognition, bio-impedance, or weight. After recognizing the user, a toilet controller or other user device may prompt a user to position one or more sensors against a torso of the user based on the toilet controller or processor within the controller recognizing or interacting with the user. The interaction may be identifying a toilet user through voice recognition, keypad input, display inputs, bio-metric impedance analysis using sensors in a toilet seat, weight sensors in a toilet seat, weight sensors in a foot scale, bio-metric finger prints, optical recognition, retinal scans, etc. A unique user ID may be determined or retrieved as a result of the user interaction. The user may be notified of a properly positioned, improperly positioned, or to move the one or more sensors to another location on the torso of the user. When the measurements are complete, a medical report may be generated and sent to a medical practitioner. The generated report may also be used to communicate health information to the toilet user. The sensors 104 may have wires 120 which run along a belt, glove, or wand; or which are imbedded within a belt, glove, or wand. The wires may connect to a wireless controller located within buckle 110. The wireless controller may process and communicate signals obtained from sensors 104 to a remote location such as a server or computer. Buckle 110 may be received by a receiving buckle 118 which is connected to toilet 116. Alternatively, the wires 120 may run along the belt in the opposite direction toward belt end 112. Belt end 112 may contain a wireless controller for receiving and transmitting signals obtained by sensors 104. Sensors 104 may obtain health data of a user while a user is sitting on the toilet or while a user is using the toilet. Health data may be more beneficial when it is obtained while a user is bearing down on a toilet while passing waste into the toilet. For example, a user's heart rate and ECG readings before, after, and while bearing down to pass waste may provide dynamic heart strain data. This information may be useful in monitoring a user's heart health condition over time enabling an early diagnosis of one or more heart conditions of a user. Similar type health measurements and health determinations may be made in relation to respirations of a user, temperature of a user, blood pressure of a user, blood flow of a user, heart rhythm of a user, heart valve conditions of a user, blood flow through arteries and veins of a user, and bronchial inflammation of a user. The health measurement data may be archived and stored in an online user library health data system. The stored data may be used to preform data analysis on sets of data relating to changes over time in user health trends and user health conditions. Neuro-networks may be trained and learn significant trends relating to data sets of each sensor and to correlations among data sets of one or more sensors. A height adjustment mechanism 114 may enable the torso belt 106 to be adjusted along a height of a user. Torso belt 106 may contain an automatic tensioner located near an end of the belt 112. Such a tensioner system may be a spring tensioner or rotational tensioner. The tensioner may help to retract the belt 106 against a user's torso 102 allowing sensors 104 to be adjacent or properly positioned for taking measurements of a toilet user using or sitting on toilet 116. The tensioner may be motorized or spring loaded. The tensioner may allow the user to lean forward in aid of using the toilet and still maintain contact with the torso belt sensors and the toilet seat lid and with sensors that may be positioned on the toilet seat lid adjacent the user's torso. When a toilet user sits on a toilet the user may be tactilely stimulated or audibly reminded to use the one or more sensors. Haptic stimulation or audible feedback may be given when the one or more torso sensors are properly positioned and tensioned and/or improperly positioned or tensioned enabling the user to adjust the belt or have an assurance of a properly positioned belt.

A user 102 may be using toilet 116 while sensors 104 are monitoring the user's heart. A toilet controller associated with the sensors may detect a heart conditions such as cardiac arrest, atrial fibrillation, cardiac dysrhythmias, or ventricular fibrillation and may inform the user that heart defibrillation is necessary. The user may or may not acknowledge and confirm defibrillation or override defibrillation. The toilet controller may then tighten the one or more torso sensors or verify a tension on the one or more torso sensors and initiate a discharge current to sensor electrodes for a controlled time and power output to reset an irregular heartbeat of the user. The toilet controller may inform the user of a successful defibrillation. The controller may also direct the user to lean forward to apply pressure to the belt if the electrodes are not making good contact with a torso of the user. An automatic torso belt tensioner may increase tension in the one or more torso sensors to obtain good contact between skin of the user and sensors on the one or more torso sensors. One or more torso sensor readings may provide feedback to a toilet controller and user about a connection or interface status of the one or more torso sensors to the user's skin. A user may be able to reposition the belt or tighten the belt to achieve an acceptable sensor interface. One or more torso sensors may be used to determine an elimination event of a user using the toilet. For example, a motion sensor or a strain sensor may detect tightening of torso muscles of a toilet user, a microphone or stethoscope may detect a user holding his or her breath while bearing down during an elimination processes, or electrode sensors may detect a heart pattern representing an elimination event. Detection on an elimination process may trigger one or more data collection systems to retrieve or correlate data that is collected from the user. An elimination event may provide a reference point in data correlation and aggregation. In another example, a user may think they are having a heart attack and sit on the toilet and attach the one or more torso sensors to determine a status of the heart. If necessary, defibrillation may take place. In another example, a person is in cardiac arrest. Another person places the person in cardiac arrest on the toilet and attached and tightens the one or more torso sensors against the torso of the cardiac arrest toilet user and commands the toilet controller to perform manual defibrillation (a shock without detecting a sinus rhythm) in an attempt restart the heart of the person in cardiac arrest.

Figure 2:
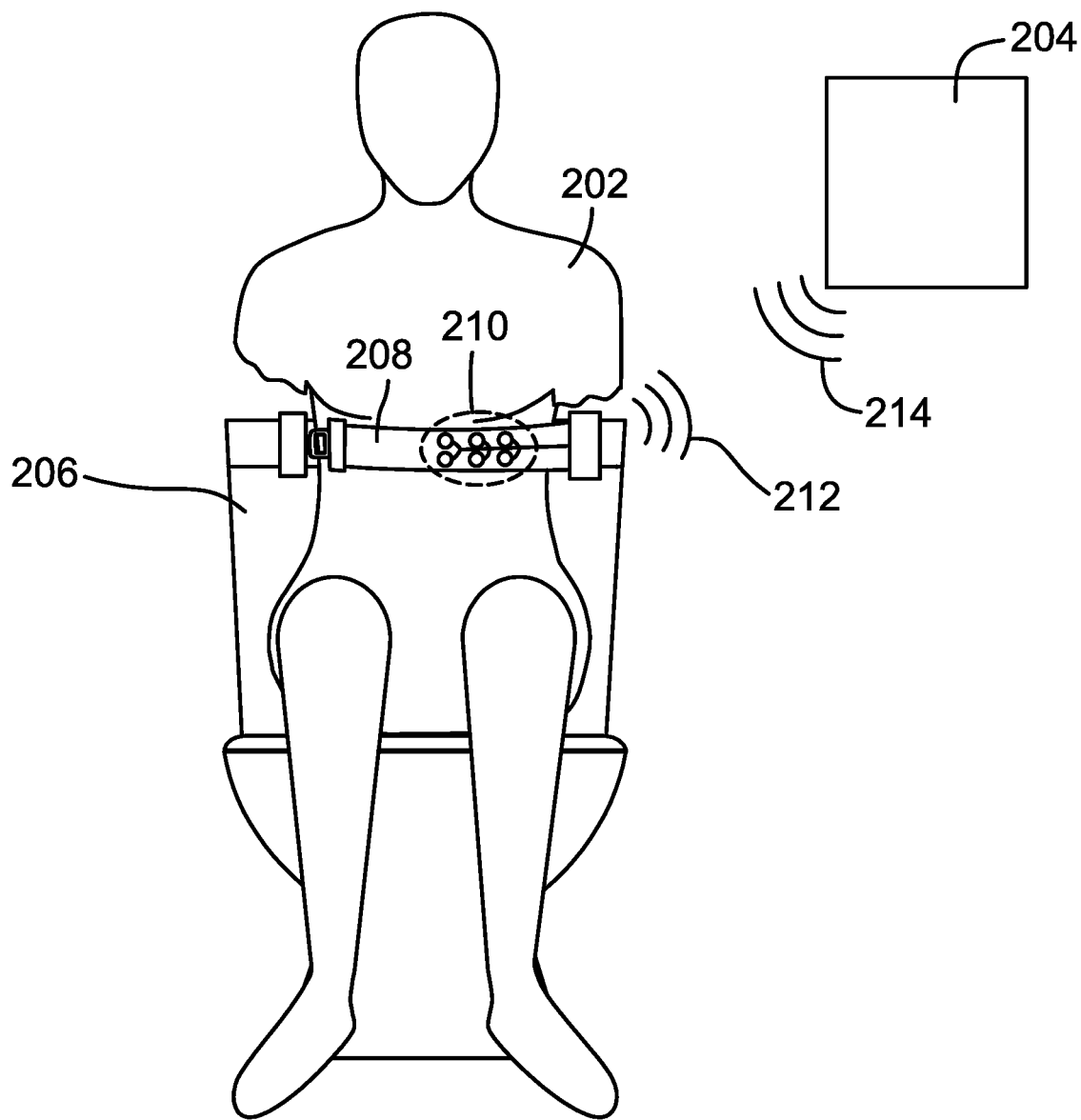
FIG. 2 is a front view of a toilet user sitting on a toilet with one or more torso sensors in accordance with an embodiment of the invention.

In FIG. 2, a user 202 is sitting on toilet 206 with a horizontal torso belt 208 horizontally stretched across the torso of user 202. The torso belt 208 contains one or more sensors 210. The sensors 210 may comprise one or more of: electrode sensors, microphone sensors, acoustic sensors, ultrasound sensors, motion sensors, strain sensors, optical sensors, temperature sensors, electrocardiogram (ECG or EKG) sensors, and/or stethoscope sensors. The sensors 210 may have wires which run along the torso belt or which are imbedded within the torso belt. The wires may connect to a wireless controller located within the toilet 206. The sensors may receive data for determining a user's temperature, respirations, heart rate, electrocardiogram, echocardiogram, and stethoscope sounds. A controller may be coupled to the sensors and programmed to determine one or more of: a user's temperature, blood pressure, respirations, heart rate, electrocardiogram, echocardiogram, and stethoscope sounds from the data received from the one or more sensors. The wireless controller may process and communicate signals 212 obtained from sensors 210 to a remote location such as a server or computer 204. Torso belt 208 may be connected to a tank 206 of the toilet. Sensors 210 may be disposable or removable sensors or have removable interfaces which couple the sensors to a user's skin or body. The removable interfaces may be ECG or EKG electrodes or other disposable sensor interfaces which provide coupling and sanitary conditions for the user.

Figure 3:
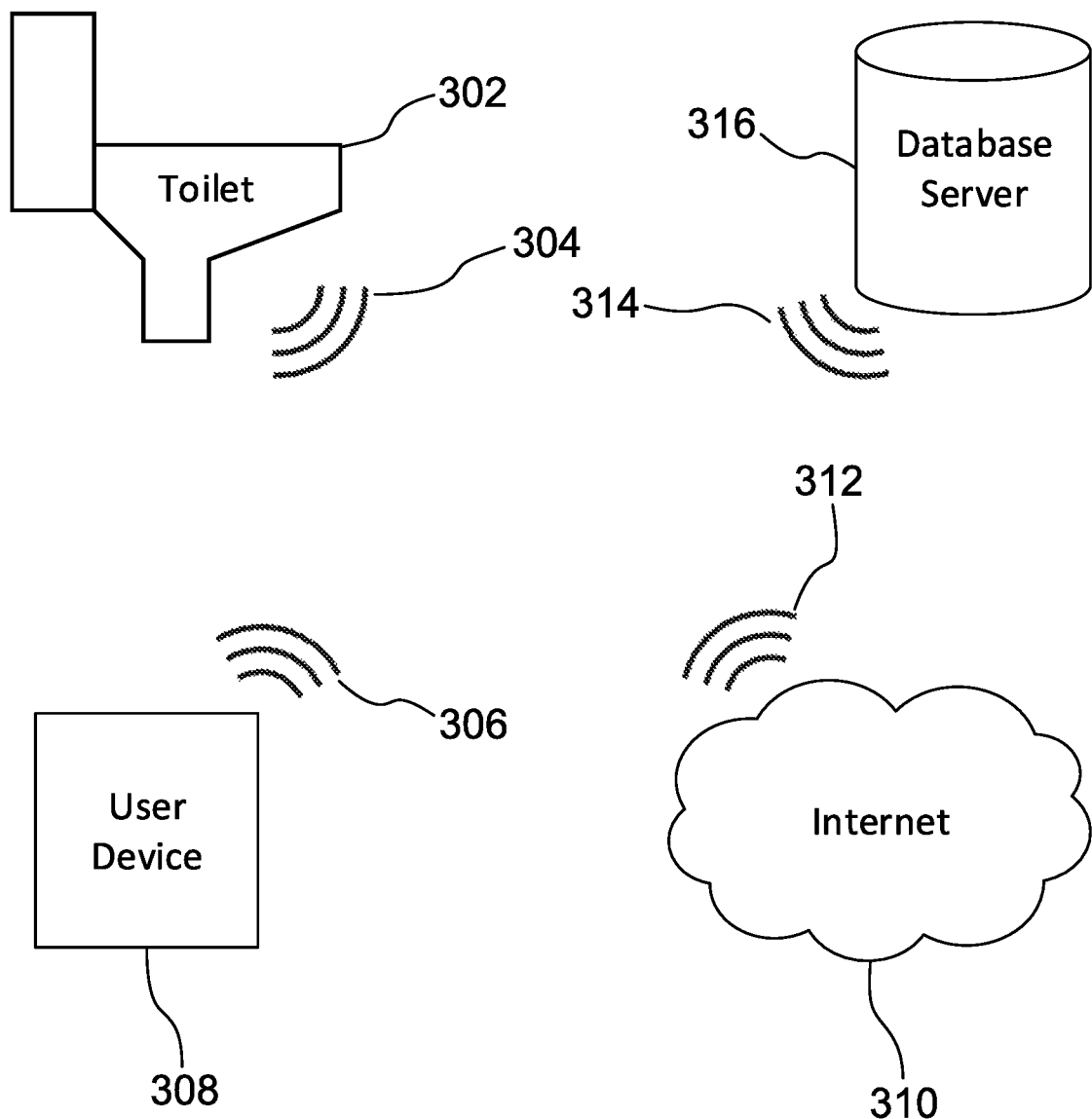
FIG. 3 a diagram showing communications between a toilet and a network in accordance with an embodiment of the invention.

In FIG. 3, a toilet 302 is able to communicate data signals to a user device 308 or to a database server 316 or to another Internet location such as a website or network address. Communication signals 304, 306, 312, and 314 may be WiFi signals, Sure-Fi signals, Bluetooth signals, near field communication signals, cellular radio signals, or a combination thereof. Toilet 302 may have a controller for gathering and transmitting health data of a user using the toilet. The health data may be gathered by means of sensors in a torso belt, glove, wand, toilet seat sensors, toilet foot sensors, and/or any combination thereof. The data may be transmitted and stored in a remote database 316, in a user device 308, or another network address of a computer or webserver. The user device may be a smart phone or tablet device.

Figure 4:
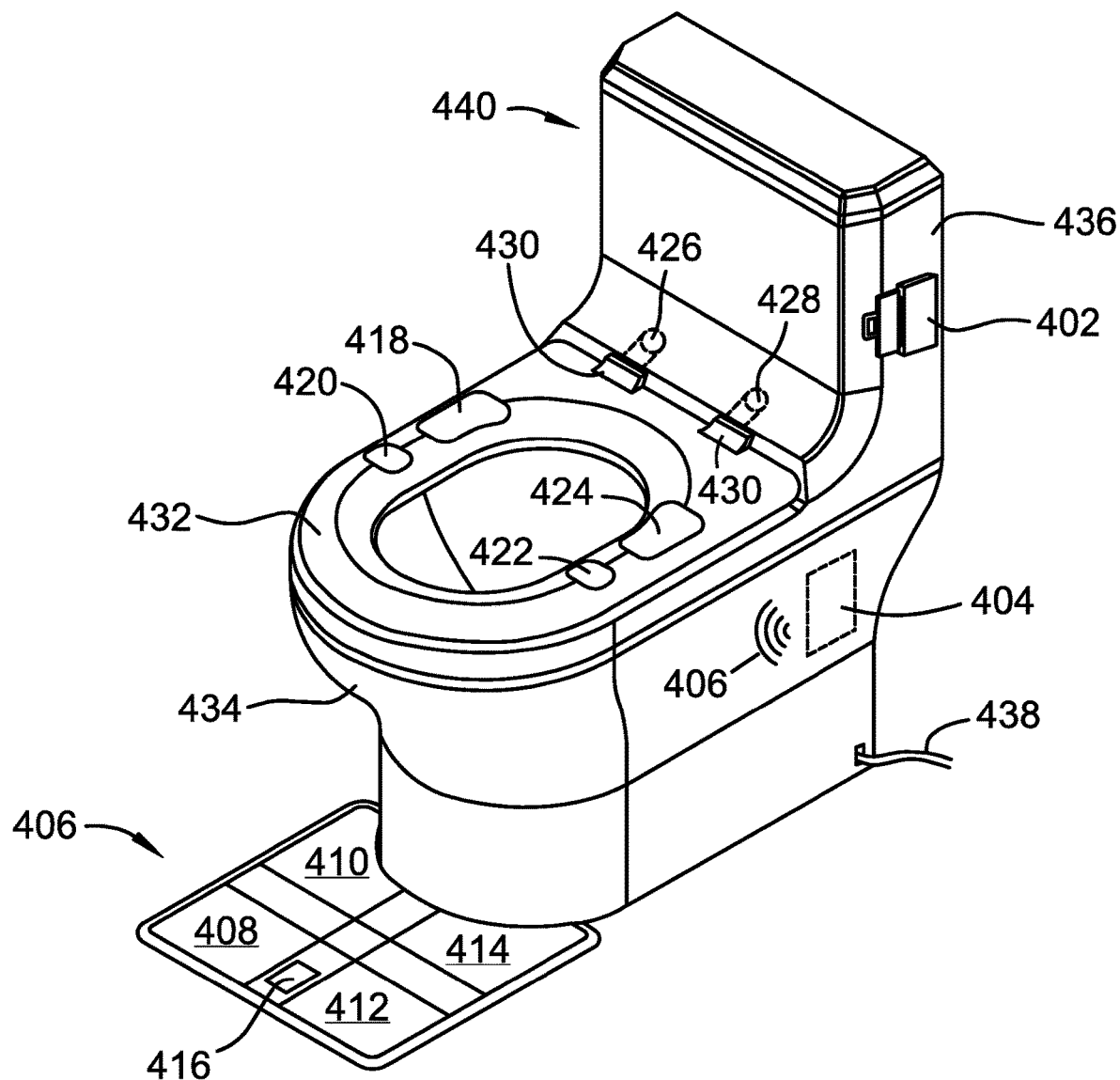
FIG. 4 is an isometric view of a toilet with one or more torso sensors in accordance with an embodiment of the invention.

In FIG. 4, a toilet 440 is shown with sensors 420, 418, 422, and 424 on toilet seat 432. The toilet seat sensors 420, 418, 422, and 424 may be used in combination with one or more torso sensors to determine health data measurements of a user. Toilet foot sensors 410, 408, 412, and 414 may be used in combination with toilet seat sensors 420, 418, 422, and 424, and/or with one or more torso sensors to determine bio-impedance health data measurements of a user. A toilet controller 404 may provide a processor and transceiver for processing sensor data and communicating the sensor data to a remote computer. The processor in the controller may interact with a toilet user. Such interaction may include voice recognition of a toilet user allowing a toilet user to provide data inputs by way of speaking. For instance, if a toilet user wanted to know what their heart rate is while using the toilet, the user may ask for their heart rate. The controller 404 may visual display or audibly speak the heart rate of the toilet user. The controller may detect a toilet user by optical sensors, motion sensors, microphones, voice recognition, bio-impedance, or weight. After recognizing the user, a toilet controller or other user device may prompt a user to position one or more torso sensors against a torso of the user based on the toilet controller or processor within the controller recognizing or interacting with the user. The interaction may be identifying a toilet user through voice recognition, keypad input, display inputs, bio-metric impedance analysis using sensors in a toilet seat, weight sensors in a toilet seat, weight sensors in a foot scale, bio-metric finger prints, optical recognition, retinal scans, etc. A unique user ID may be determined or retrieved as a result of the user interaction. The user may be notified of properly positioned or improperly positioned sensor, or to move the one or more torso sensors to another location on the torso of the user. When the measurements are complete, a medical report may be generated and sent to a medical practitioner. The generated report may also be used to communicate health information to the toilet user. Controller 404 may communicate wirelessly or by wire to other computer or network devices.

Torso belt 402 contains one or more torso sensors which are stretched across a user while the user is using toilet 440. Toilet 440 also may include strain sensors 426 and 428 for determining a weight of a user or to detect that a user is sitting on the toilet. After a user is detected as sitting on the toilet a toilet controller may prompt a user to install or put on the one or more torso sensors. The prompting may be audible sound such as a speaker transmitting recorded audio instructions on how to attach the one or more sensors and/or reminding the user to install the one or more sensors. The prompting may also be haptic stimulation such as a seat that vibrates or a seat lid that vibrates or makes noise reminding the user to install or put on the one or more sensors. The prompting may also be a visual indicator such as a light build into the side of the toilet or a user screen of a toilet. After the one or more sensors is installed, a notification of a successful interface between the sensors and the user's body may be given as an audible sound, visual indicator or haptic stimulation. For example, if a one or more sensors is not tight enough against the user's skin, a red light or particular noise may indicate that the belt is not properly interfaced with the user's skin. If the one or more sensors is making good contact and positioned properly, the light on the toilet may turn green and/or a particular sound may be generated indicating a good position and connection of the sensors on the belt. Strain sensors 426 and 428 may be used in combination with strain sensors located within foot scale device 406 to determine an overall weight of a toilet user. Torso Belt 402 may stretch across a user while the user is sitting on the toilet base 434 and the torso belt may connect to a receiving buckle on an opposite side of tank 436.

Figure 5:
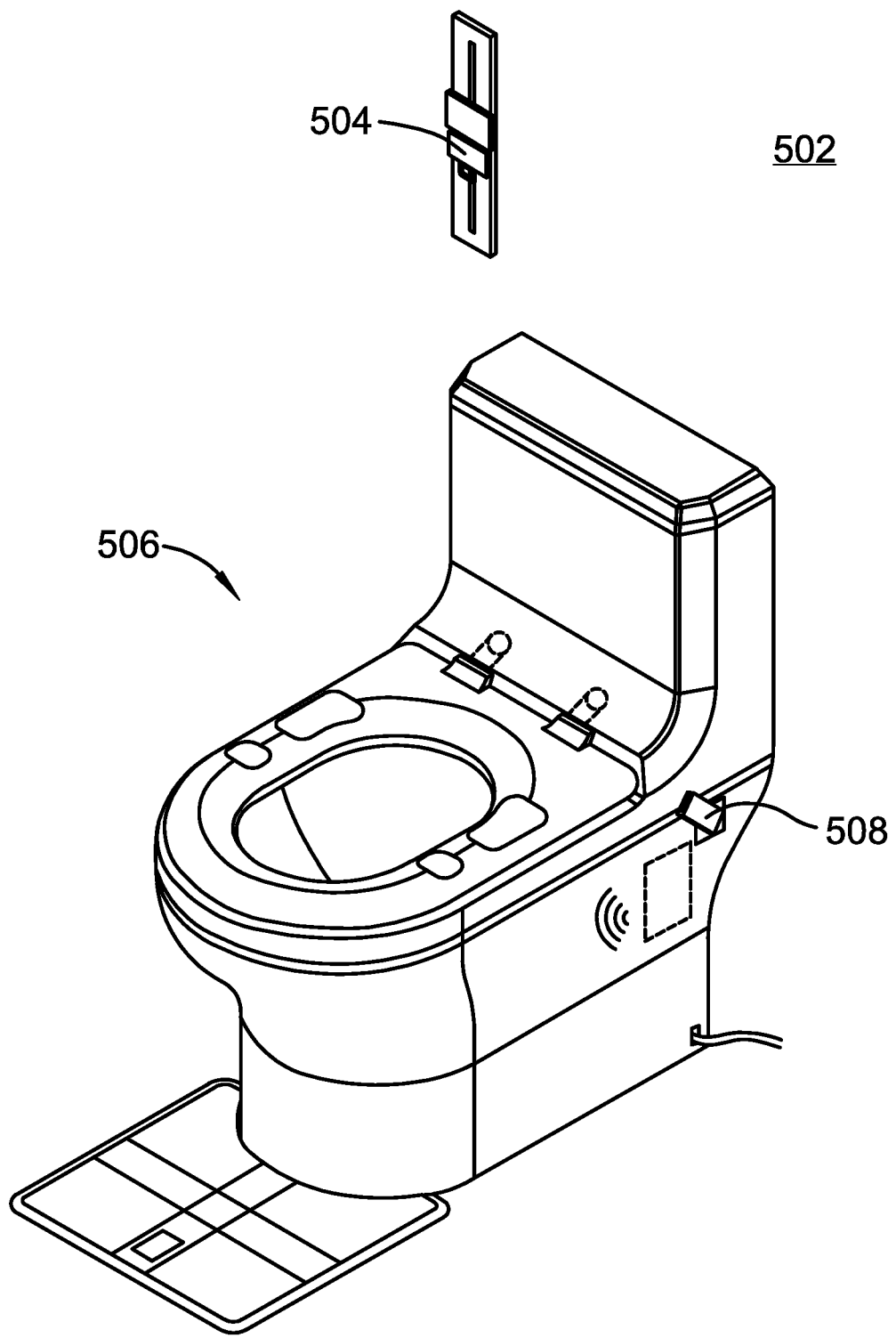
FIG. 5 is an isometric view of a toilet with one or more torso sensors in accordance with an embodiment of the invention.

FIG. 5 show a similar toilet to FIG. 4 except the torso belt 504 is now located on a bathroom wall 502 along with the height adjustment mechanism. The receiving buckle 508 is shown fixed to a toilet base section. The placement of the receiving buckle 508 allows the one or more sensors to be extended in a diagonal across a toilet user while the toilet user is sitting on the toilet.

Figure 6:
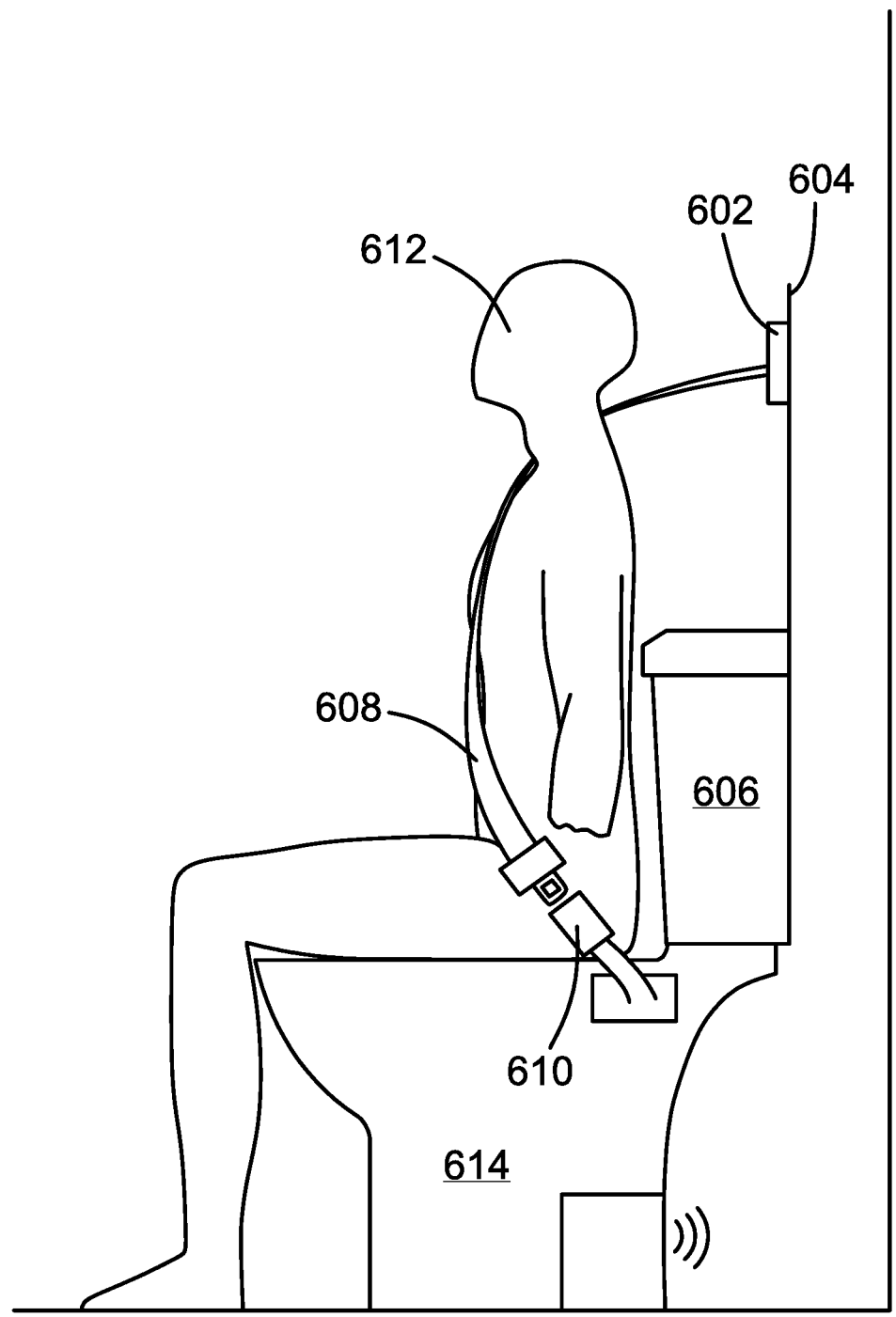
FIG. 6 is a side view of a toilet user sitting on a toilet with one or more torso sensors in accordance with an embodiment of the invention.

In FIG. 6, a toilet user 612 is sitting on toilet base section 614 with one or more sensors diagonally extended across the user's torso. One or more sensors may be connected to a tensioning device 602 which is attached to toilet tank 606. The tensioning device 602 may optionally be attached to a bathroom wall as shown in FIG. 5. One or more sensors may also be attached to a toilet user wand or glove. A user may be directed to position and apply pressure using the wand or glove while obtaining health measurements in order to get acceptable readings.

Figure 7:
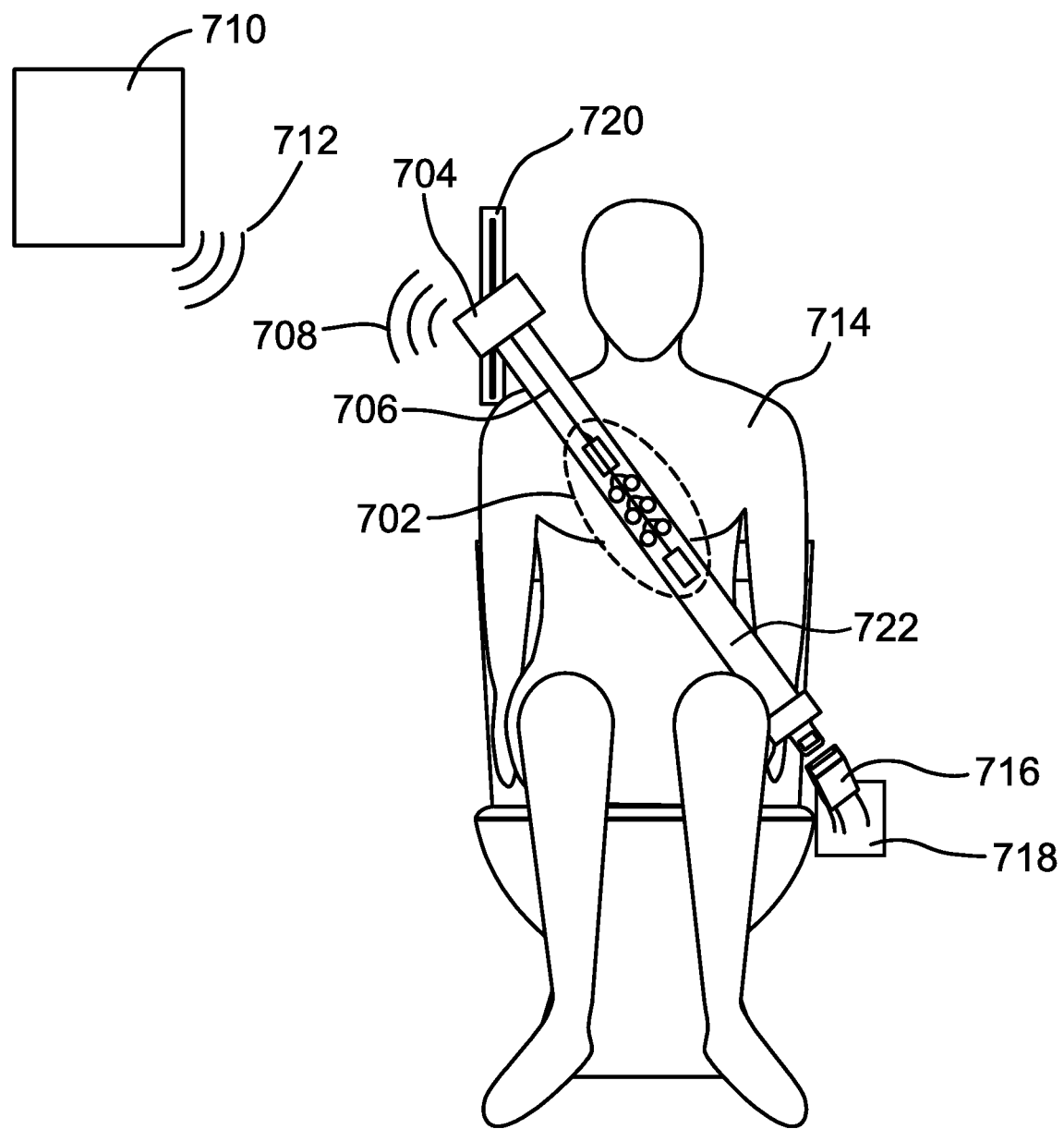
FIG. 7 is a front view of a toilet user sitting on a toilet with one or more torso sensors in accordance with an embodiment of the invention.

In FIG. 7, a toilet user 714 is using a toilet to eliminate waste by bearing down and pushing the waste out. As the user is bearing down, motion sensors or strain sensors 702 may detect and send signals indicative of the user bearing down to wireless controller 704. Upon receiving an indication of the user bearing down, the controller starts obtaining ECG readings of the user to monitor the user's heart as stress is applied to the heart from the user bearing down to eliminate waste. Controller 704 may record in memory or transmit to a remote storage device data obtained from sensors 702. The sensors 702 may comprise one or more of: electrode sensors, microphone sensors, acoustic sensors, ultrasound sensors, motion sensors, strain sensors, optical sensors, temperature sensors, electrocardiogram (ECG or EKG) sensors, and/or stethoscope sensors. The sensors may receive data for determining a user's temperature, blood pressure, respirations, heart rate, electrocardiogram, echocardiogram, and stethoscope sounds. A controller may be coupled to the sensors and programmed to determine one or more of: a user's temperature, respirations, heart rate, electrocardiogram, echocardiogram, and stethoscope sounds from the data received from the one or more sensors. A processor in the controller may interact with a toilet user. Such interaction may include voice recognition of a toilet user allowing a toilet user to provide data inputs by way of speaking. For instance, if a toilet user wanted to know what their heart rate is while using the toilet, the user may ask for their heart rate. The controller may visual display or audibly speak the heart rate of the toilet user. The controller may detect a toilet user by optical sensors, motion sensors, microphones, voice recognition, bio-impedance, or weight. After recognizing the user, a toilet controller or other user device may prompt a user to position one or more sensors against a torso of the user based on the toilet controller or processor within the controller recognizing or interacting with the user. The interaction may be identifying a toilet user through voice recognition, keypad input, display inputs, bio-metric impedance analysis using sensors in a toilet seat, weight sensors in a toilet seat, weight sensors in a foot scale, bio-metric finger prints, optical recognition, retinal scans, etc. A unique user ID may be determined or retrieved as a result of the user interaction. The user may be notified of properly positioned or improperly positioned sensors, or to move the one or more sensors to another location on the torso of the user. When the measurements are complete, a medical report may be generated and sent to a medical practitioner. The generated report may also be used to communicate health information to the toilet user. The sensors 702 may have wires which run along the torso belt or which are imbedded within the torso belt. The wires may connect to a wireless controller located within the toilet or to wireless controller 704. The wireless controller 704 may process and communicate signals 708 obtained from sensors 702 to a remote location such as a server or computer 710. The data may be stored in connection to a user or user profile. The data may be used for health monitoring purposes and may be evaluated by remotely located physicians. A receiving buckle end 716 may be connected to a bathroom wall or to the toilet. The sensors 702 may include transmit receive pairs, transducers, transmitters, electrodes, optical transmitters and receivers, ultrasonic transmitters and receivers, acoustic transmitters and receivers, etc.

Figure 8:
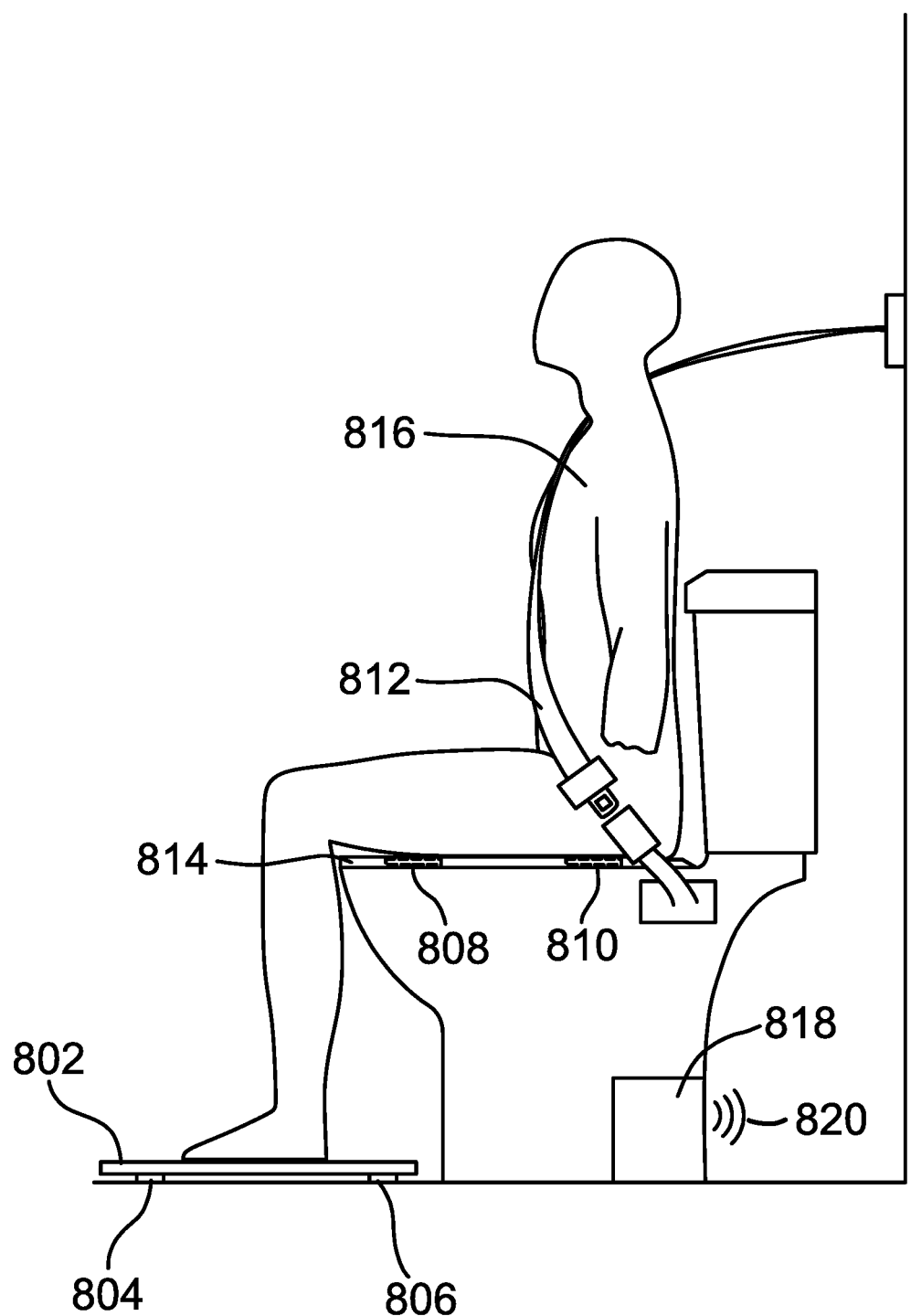
FIG. 8 is a side view of a toilet user sitting on a toilet with one or more torso sensors in accordance with an embodiment of the invention.

In FIG. 8, a toilet user 816 is positioned on a toilet with torso belt 812 diagonally positioned across the user's torso 816. The user's bottom and thighs are touching sensors 808 and 810 embedded in the toilet seat 814 and the user's feet are touching bio-metric electrodes on the surface 802 of the foot scale. The foot scale contains two or more strain sensors 804 and 806 for determination of a weight of a user using the toilet. The user's weight may be determined in part by strain sensors which are located on or near toilet seat 814 and on or near scale surface 802. A wireless toilet controller 818 may be in wireless or wired communication with toilet seat 814, one or more sensors 812, and/or foot scale 802. The toilet controller may obtain health measurement data related to a user's health and report the data to an online repository or network data base location. The data may include: bio-impedance electrode sensor data, microphone sensor data, acoustic sensor imaging data, ultrasound imaging sensor data, motion sensor data, strain sensor data, optical sensor data, temperature sensor data, electrocardiogram (ECG or EKG) sensor data, and/or stethoscope noise data.

User health data may be sampled and stored in a remote database. The stored data may be used to create a rolling history and rolling averages of health conditions of a toilet user. Rolling averages of heart rate, blood pressure, temperature, respirations of a user, blood flow, heart rate while eliminating waste, bio-impedance, hydration levels, heart valve function, etc. may be mapped over time and significant changes to a rolling average may be flagged for review by a physician or automatically sent to the user's doctor.

Figure 9:
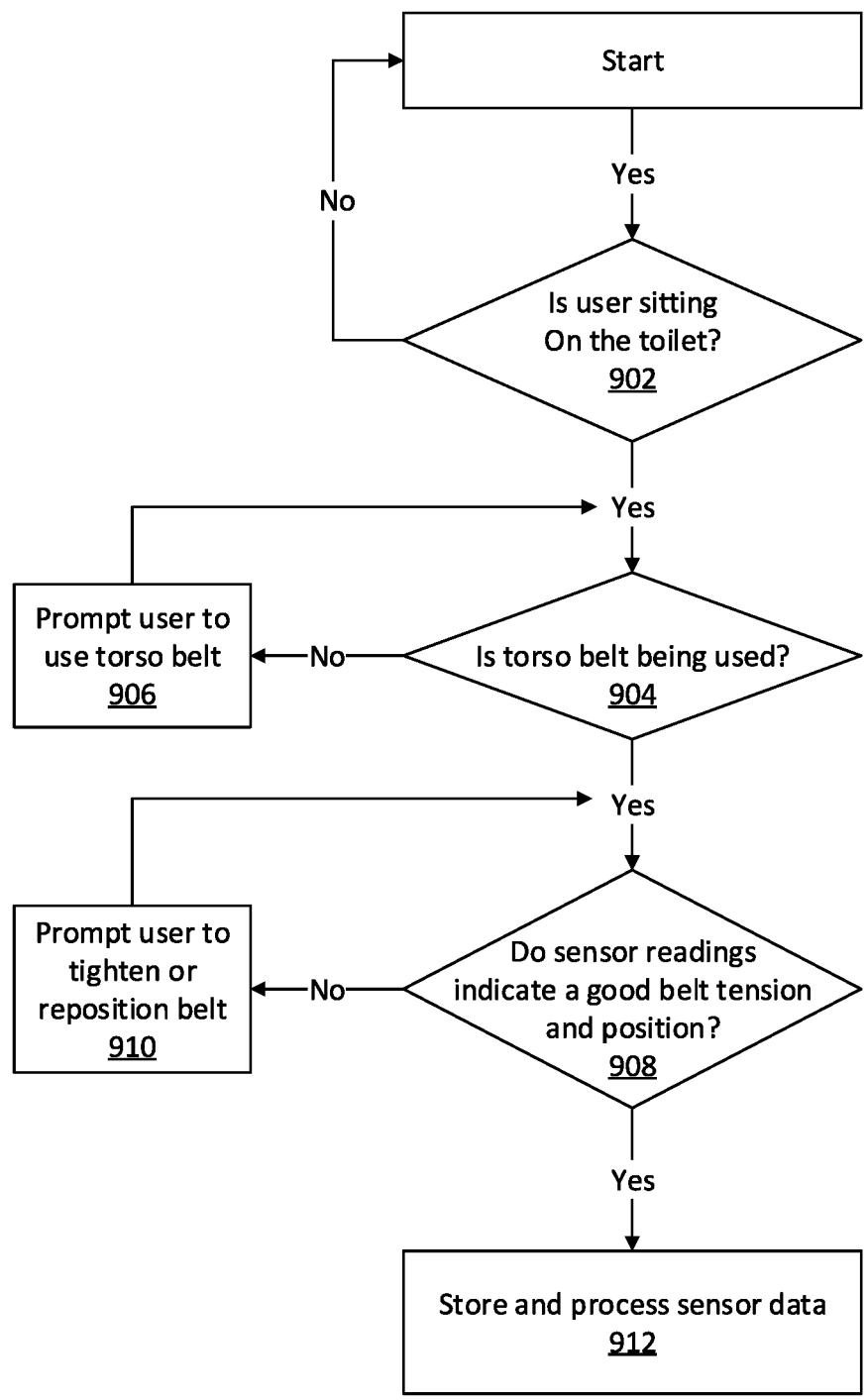
FIG. 9 is a flow diagram of obtaining heath measurements of a toilet user in accordance with an embodiment of the invention.

In FIG. 9, a process of obtaining user health data starts by a user sitting on a toilet and the toilet detects the user 902. The user detection process is described in application Ser. No. 15/150,797 titled "User Identifying Toilet Apparatus" by the same inventors as the instant application. User identification may be determined by bio-impedance sensors located on the toilet seat and/or foot scale of the toilet as shown in FIGS. 4, 5, and 8 of the instant application. Force sensors may also be used to identify a user or user presence on the toilet seat. One or more microphone may also be used to detect a presence of a user. Optical sensors in the toilet seat may also be used to detect a presence of a user on the seat. In process step 904, a toilet controller may make a determination if a toilet user has put on the one or more sensors. It the user has not put on the one or more sensors the controller may audibly or tactilely remind the user to put on the one or more sensors 906. Preprogrammed or recoded voice information may be relayed by a speaker to the toilet user. The toilet seat may also be vibrated or jolted to remind a user to install the one or more sensors. In process step 908 a determination is made if the sensors are reading good data indicating that the one or more sensors are positioned correctly and tight enough. If the sensor reading are not valid or inconsistent a user may be prompted to tighten or reposition the one or more sensors. Alternatively, or additionally, the one or more sensors may be automatically tensioned using a tensioning motor to try to improve sensor readings on the one or more sensors. When the sensor readings are good 912, the sensor data is stored and processed for trend analysis and data analysis.

Figure 10:
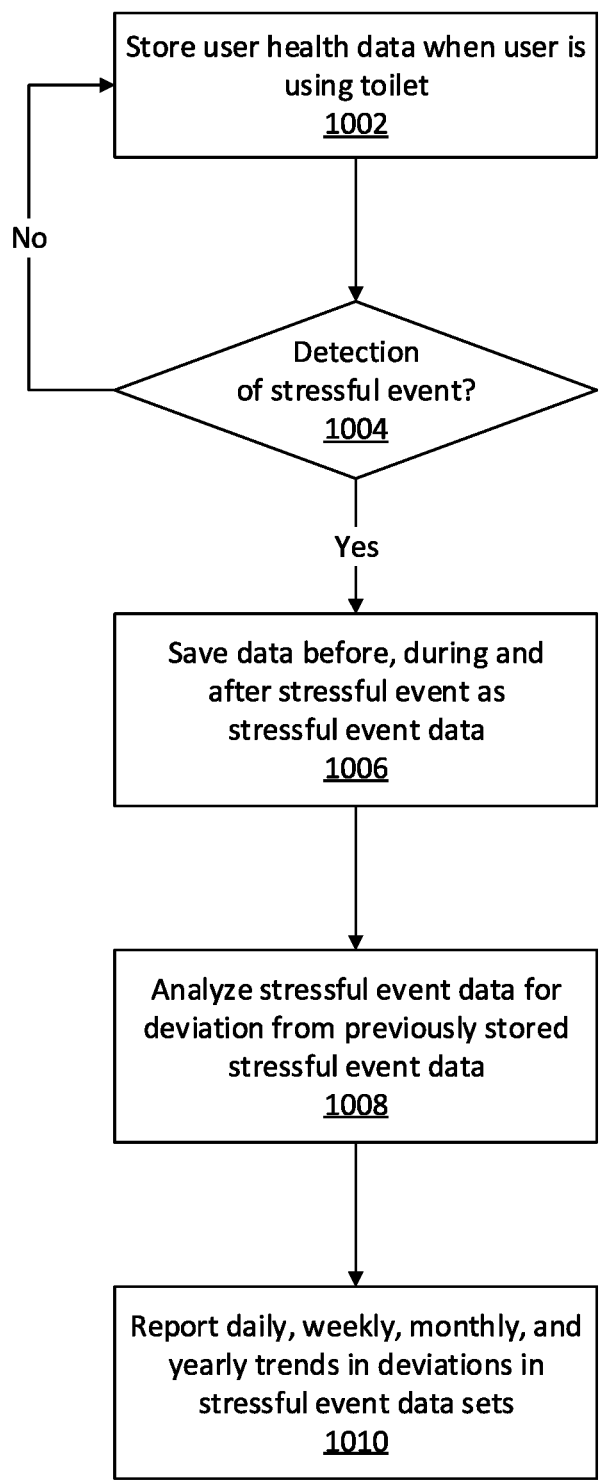
FIG. 10 is a flow diagram of user interaction with a toilet in accordance with an embodiment of the invention.

In FIG. 10, the data is being stored and monitored for a stressful event detection 1004. A stressful event may be contractions of a pregnant user, a bowel movement event of a user, or a painful event of any kind while a user is using the toilet. The stressful event may be determined based on heart rate, blood pressure, strain sensor readings, microphone data, stethoscope data, optical sensor data, ultrasound sensor data, bio-metric sensor data, electrode sensor data, acoustic sensor data, imaging data, or temperature data. When a stressful event is determined, a new data collection process 1006 takes place and data is captured previous to the stressful event, during the stressful event, and when the stressful event ends or when the user leaves the toilet if the user is still under stress when they leave the toilet. In process step 1008, the stressful data collected is compared to previously stressful event data sets to determine if the current stressful data deviates more than a predetermined amount from the historical stressful data sets collected. If the new stressful event data deviates more than a predetermined amount from the historical stressful data sets then one or more notifications may be sent out. Notifications may be in the form of emails, text messages, or the reporting of the data to outside computers or networks or health care systems. Trends which also fall outside of a predetermined range may also trigger notifications in the form of emails, text messages, or the reporting of the data to outside computers or networks or health care systems.

Figure 11:
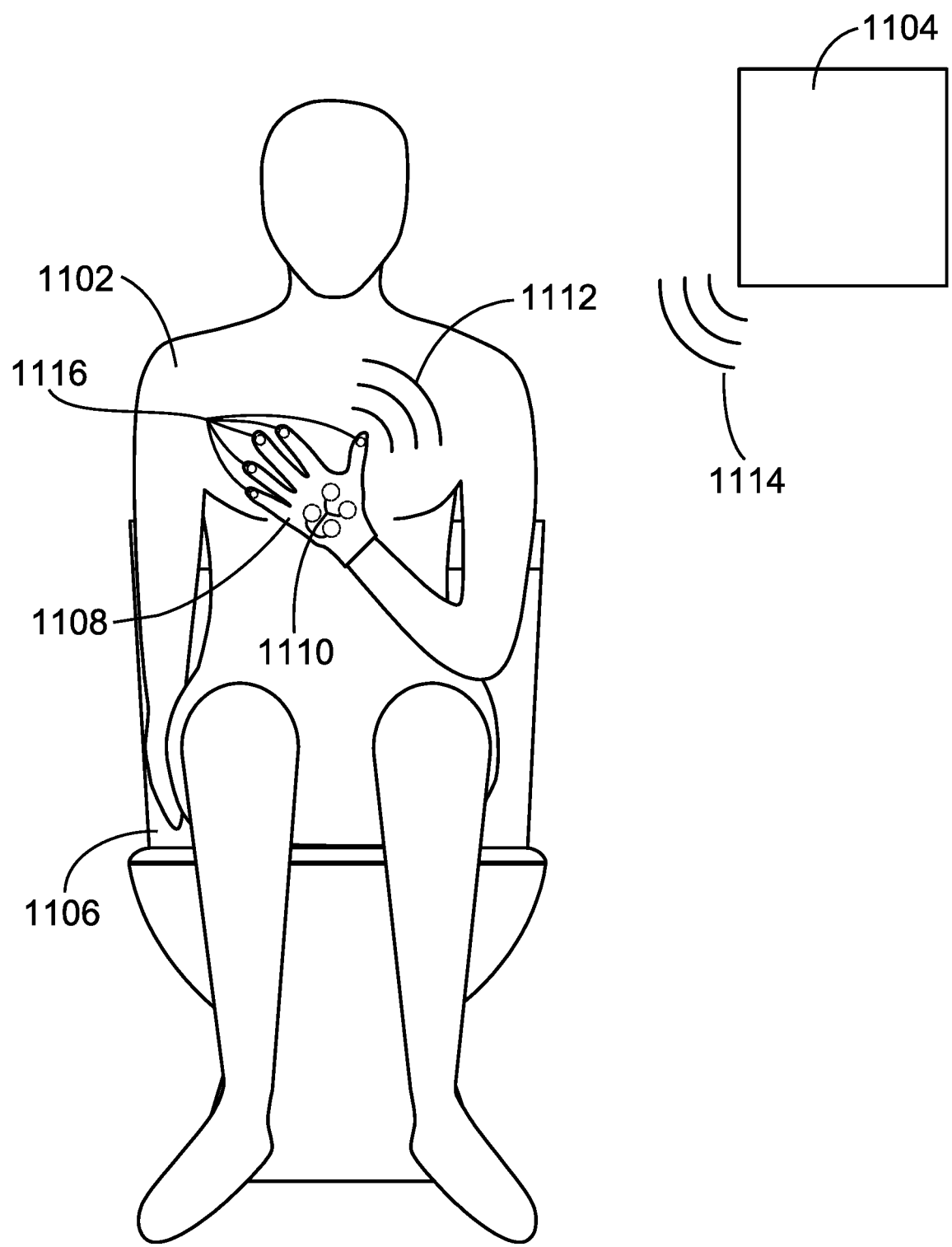
FIG. 11 is a front view of a toilet user sitting on a toilet with one or more torso sensors attached to a glove in accordance with an embodiment of the invention.

In FIG. 11, a user 1102 is sitting on toilet 1106 with a with a glove 1108 positioned on the torso of user 1102. The glove 1108 contains one or more sensors 1110. The sensors 1110 may comprise one or more of: electrode sensors, microphone sensors, acoustic sensors, ultrasound sensors, motion sensors, strain sensors, optical sensors, temperature sensors, electrocardiogram (ECG or EKG) sensors, and/or stethoscope sensors. The sensors 1110 may have wires which connect to an imbedded wireless communication device within the glove. A wireless signal 1112 may report sensor data to a remote computer 1104. The remote computer may be a toilet computer or other remote computer system. The wires may connect to a wireless controller located within the toilet 1106. The sensors 1110 may have wires which are directly connected to a toilet computer or processor. The sensors 1110 may receive data for determining a user's temperature, respirations, heart rate, oxygen concentration, blood pressure, electrocardiogram, echocardiogram, and stethoscope sounds. A controller 1104 may be coupled to the sensors and programmed to determine one or more of: a user's temperature, blood pressure, respirations, heart rate, electrocardiogram, echocardiogram, and stethoscope sounds from the data received from the one or more sensors. Controller 1104 may be a wireless controller and may process and communicate signals 1112 obtained from sensors 1110 to a remote location such as a server or computer. Glove 1108 may be connected to a hand of a toilet user. Sensors 1110 may be disposable or removable sensors or have removable interfaces which couple the sensors to a user's skin or body. The removable interfaces may be ECG or EKG electrodes or other disposable sensor interfaces which provide coupling and sanitary conditions for the user. The sensors 1110 in glove 1108 may work in a similar fashion as described in relation to FIGS. 7, 9 and 10. Glove 1108 may have internal sensors 1116 for measuring a hand of a user. Sensors 1116 may be used to measure a user's temperature, respirations, heart rate, oxygen concentration and/or blood pressure in addition to or instead of torso measurements.

Figure 12:
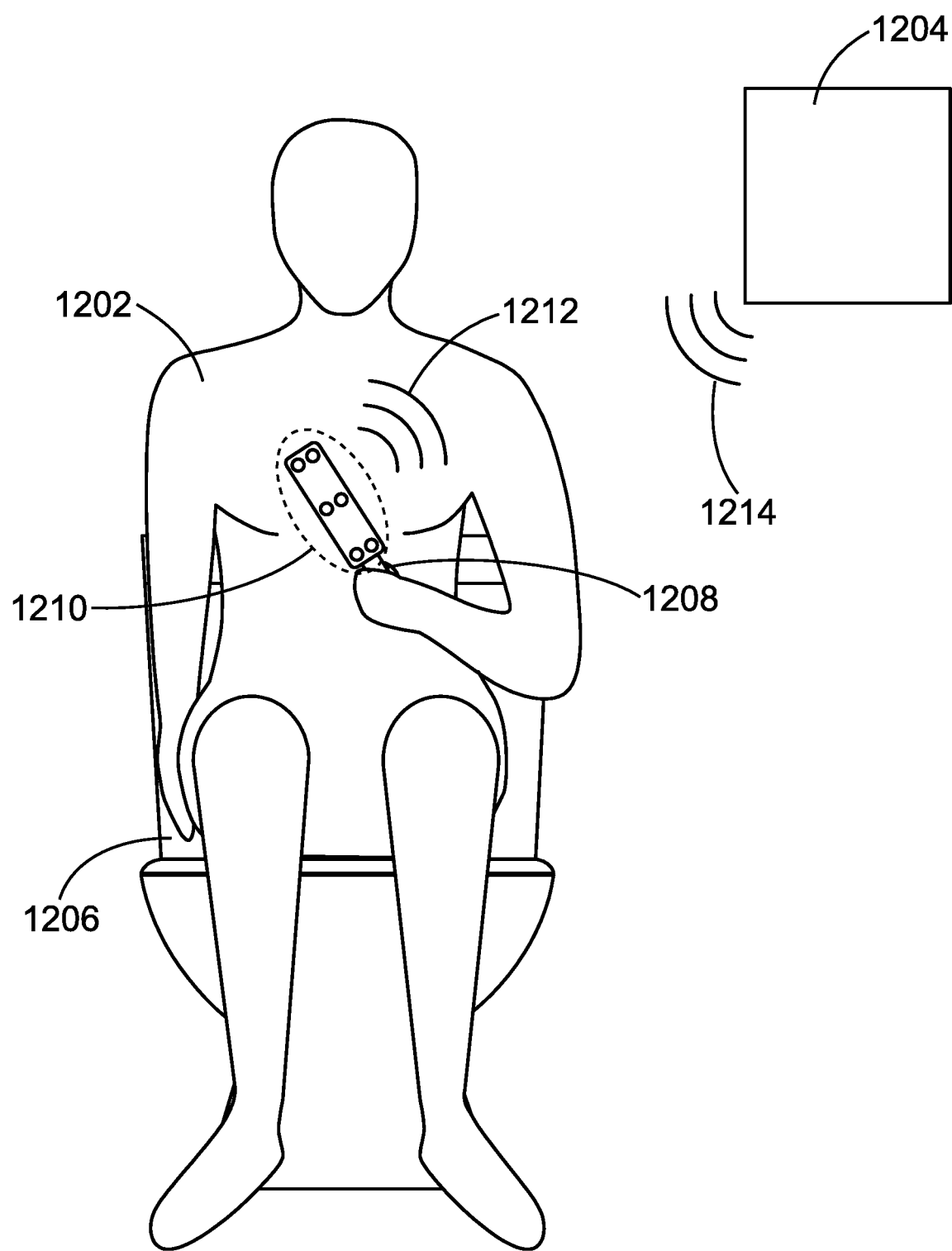
FIG. 12 is a front view of a toilet user sitting on a toilet with one or more torso sensors attached to a wand in accordance with an embodiment of the invention.

In FIG. 12, a user 1202 is sitting on toilet 1206 with a with a wand 1208 positioned on the torso of user 1202. The wand 1208 contains one or more sensors 1210. The sensors 1210 may comprise one or more of: electrode sensors, microphone sensors, acoustic sensors, ultrasound sensors, motion sensors, strain sensors, optical sensors, temperature sensors, electrocardiogram (ECG or EKG) sensors, and/or stethoscope sensors. The sensors 1210 may have wires which connect to an imbedded wireless communication device within the wand. A wireless signal 1212 may report sensor data to a remote computer 1204. The remote computer may be a toilet computer or other remote computer system. The wires may connect to a wireless controller located within the toilet 1206. The sensors 1210 may have wires which are directly connected to a toilet computer or processor. The sensors 1210 may receive data for determining a user's temperature, respirations, heart rate, oxygen concentration, blood pressure, electrocardiogram, echocardiogram, and stethoscope sounds. A controller 1204 may be coupled to the sensors and programmed to determine one or more of: a user's temperature, blood pressure, respirations, heart rate, electrocardiogram, echocardiogram, and stethoscope sounds from the data received from the one or more sensors. Controller 1204 may be a wireless controller and may process and communicate signals 1212 obtained from sensors 1210 to a remote location such as a server or computer. Wand 1208 may be connected to a hand of a toilet user. Sensors 1210 may be disposable or removable sensors or have removable interfaces which couple the sensors to a user's skin or body. The removable interfaces may be ECG or EKG electrodes or other disposable sensor interfaces which provide coupling and sanitary conditions for the user. The sensors 1210 in wand 1208 may work in a similar fashion as described in relation to FIGS. 7, 9 and 10. Wand 1208 may have internal sensors (not shown, located on the hand grip of wand 1208) for measuring a hand of a user. Hand grip sensors (not shown) may be used to measure a user's temperature, respirations, heart rate, oxygen concentration and/or blood pressure in addition to or instead of torso measurements.

Figure 13:
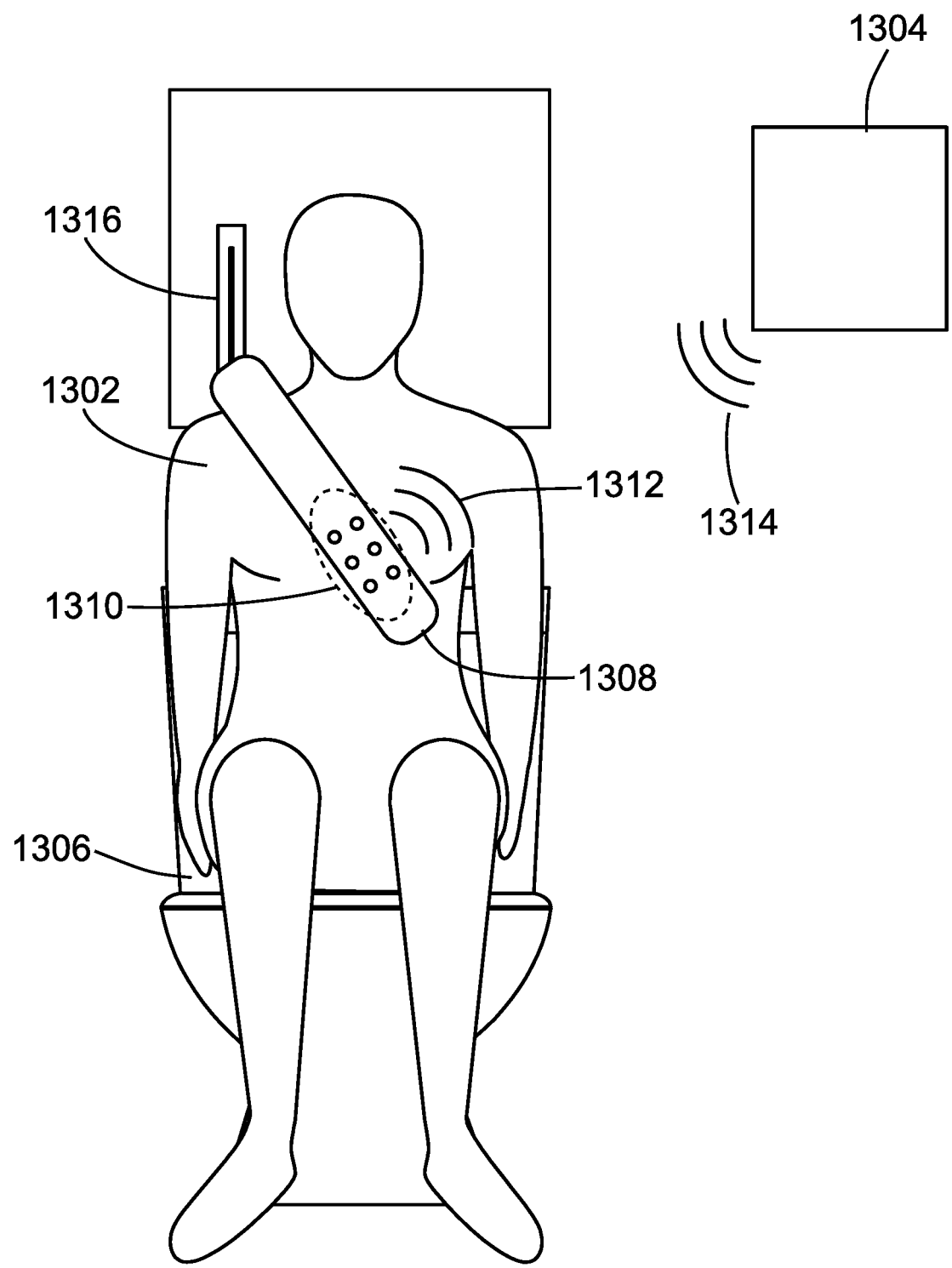
FIG. 13 is a front view of a toilet user sitting on a toilet with one or more torso sensors attached to a mechanical arm in accordance with an embodiment of the invention.

In FIG. 13, a user 1302 is sitting on toilet 1306 with a with a mechanical arm 1308 positioned on the torso of user 1302. The mechanical arm 1308 contains one or more sensors 1310. The sensors 1310 may comprise one or more of: electrode sensors, microphone sensors, acoustic sensors, ultrasound sensors, motion sensors, strain sensors, optical sensors, temperature sensors, electrocardiogram (ECG or EKG) sensors, and/or stethoscope sensors. The sensors 1310 may have wires which connect to an imbedded wireless communication device within the mechanical arm. A wireless signal 1312 may report sensor data to a remote computer 1304. The remote computer may be a toilet computer or other remote computer system. The wires may connect to a wireless controller located within the toilet 1306. The sensors 1310 may have wires which are directly connected to a toilet computer or processor. The sensors 1310 may receive data for determining a user's temperature, respirations, heart rate, oxygen concentration, blood pressure, electrocardiogram, echocardiogram, and stethoscope sounds. A controller or computer 1304 may be coupled to the sensors and programmed to determine one or more of: a user's temperature, blood pressure, respirations, heart rate, electrocardiogram, echocardiogram, and stethoscope sounds from the data received from the one or more sensors. Controller 1304 may be a wireless controller and may process and communicate signals 1312 obtained from sensors 1310 to a remote location such as a server or computer. Mechanical arm 1308 may be connected to a hand of a toilet user. Sensors 1310 may be disposable or removable sensors or have removable interfaces which couple the sensors to a user's skin or body. The removable interfaces may be ECG or EKG electrodes or other disposable sensor interfaces which provide coupling and sanitary conditions for the user. The sensors 1310 in mechanical arm 1308 may work in a similar fashion as described in relation to FIGS. 7, 9 and 10. A height adjustment mechanism 1316 may allow mechanical arm 1308 to be adjusted according to a torso height of user 1302. Mechanical arm 1308 may be able to be rotated or pivoted around the chest of user 1302. Mechanical arm 1308 may be pressed against a chest of user 1302 by means of an electrical motor applying rotational force about a pivot of mechanical arm 1308. A rotational force may also be applied to mechanical arm 1308 by means of a spring or springing material.

The toilet and methods disclosed herein may be embodied in other specific forms without departing from their spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of monitoring health of a user comprising:
   providing a toilet with one or more sensors;
   during each use of the toilet by the user, generating data based on signals from the one or more sensors, the data being indicative of at least one health factor of the user;
   collecting the generated data from each use in a use data set;
   calculating rolling averages from the data sets; and
   mapping the rolling averages, identifying any significant changes, and flagging the significant changes for review.

2. The method of claim 1, wherein the one or more sensors comprises one or more electrocardiogram sensors, ultrasonic imaging sensors, temperatures sensors, optical sensors, strain sensors, bio-impedance sensors, microphones, stethoscopes, or acoustic imaging sensors.

3. The method of claim 1, further comprising detecting a stressful event based on data obtained from the one or more sensors.

4. The method of claim 3, wherein the stressful event is one or more of: uterine contractions, bowels contractions, heart rhythm irregularities, blood flow irregularities, breathing irregularities, irregular blood pressure, high temperature, muscle tightening, low temperature, vocal sound combinations indicating pain, vocal sound combinations indicating a need for help, or vocal sound combinations indicating a need for medical attention.

5. The method of claim 3, wherein the data is stored and compared to previously stored stressful event data sets.

6. The method of claim 5, further comprising transmitting one or more notifications when stressful event data changes by a predetermined threshold compared to the previously stored stressful event data sets.

7. The method of claim 1, further comprising notifying the toilet user using one or more visual notifications, audio notifications, or haptic notifications.

8. The method of claim 1, further comprising prompting the toilet user by displaying instruction to the toilet user on a display.

9. The method of claim 8, wherein the instructions include visual sensor placement instructions.

10. The method of claim 1, wherein the one or more sensors contain wires connecting the one or more sensors to a wireless transceiver.

11. The method of claim 1, wherein the one or more sensors further comprise removable electrodes.

12. The method of claim 11, wherein the removable electrodes are used to obtain both electrocardiogram measurements and bio-impedance measurements.

13. The method of claim 1, wherein changes to the users rolling average are flagged to alert a physician to review the user's data sets and the change to the user's rolling average.

14. The method of claim 1, further comprising: identifying, with the one or more sensors when a user is bearing down during an elimination event to pass waste into the toilet and utilizing the elimination event as a reference point for correlating and aggregating the data-sets.

15. The method of claim 1 wherein at least one of the one or more health sensors is located on a torso belt.

16. The method of claim 15, wherein the one or more sensors diagonally extend or horizontally extend across the torso of the toilet user.

17. The method of claim 15, wherein the notifying of the toilet user includes instructing the toilet user to move the one or more sensors to another location on the toilet user's torso for additional data collection.

18. The method of claim 15, wherein the notifying of the toilet user includes instructing the toilet user to apply pressure to the one or more sensors against the torso of the toilet user.

19. The method of claim 15 further comprising toilet seat sensors, wherein the medical report is a result of the toilet seat sensors and the one or more sensors against the torso of the toilet user.

20. The method of claim 19 further comprising foot sensors, wherein the medical report is a result of the toilet seat sensors, the foot sensors, and the one or more sensors against the torso of the toilet user.

21. The method of claim 19, wherein the removable electrodes are used to defibrillate a heart of the toilet user while sitting on the toilet.

* * * * *